United States Patent [19]

Berg

[11] Patent Number: 5,320,715
[45] Date of Patent: Jun. 14, 1994

[54] SEPARATION OF 1-PENTANOL FROM CYCLOPENTANOL BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 181,017

[22] Filed: Jan. 14, 1994

[51] Int. Cl.$^5$ .................... B01D 3/40; C07C 29/84
[52] U.S. Cl. .................................. 203/57; 203/58; 203/64; 568/913; 568/918
[58] Field of Search .................... 203/64, 57, 58, 56, 203/51; 568/913, 918

[56] References Cited

U.S. PATENT DOCUMENTS 2,551,584  5/1951  Carlson et al. ............... 203/58
3,310,478  3/1967  Amir ............................ 203/64
4,969,977  11/1990  Berg ............................ 203/65

*Primary Examiner*—Wilbur Bascomb, Jr.

[57] ABSTRACT

1-Pentanol is difficult to separate from cyclopentanol by conventional distillation or rectification because of the closeness of their boiling points. 1-Pentanol can be readily separated from cyclopentanol by extractive distillation. Effective agents are ethylene glycol and sulfolane.

1 Claim, No Drawings

SEPARATION OF 1-PENTANOL FROM CYCLOPENTANOL BY EXTRACTIVE DISTILLATION

FIELD OF THE INVENTION

This invention relates to a method for separating 1-pentanol from cyclopentanol using certain lower boiling liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component. At the bottom of a continuous column, the less volatile components of the close boiling mixtures and the extractive agent are continuously removed from the column. The usual methods of separation of these two components are the use of another rectification column, cooling and phase separation, or solvent extraction. 1-Pentanol boils at 138° C.; cyclopentanol boils at 140° C. Although they do not form an azeotrope with each other, the closeness of their boiling points give them a relative volatility of 1.15. Table 1 shows the relative volatility required to get 99% purity. By straight rectification, 88 actual plates are required for the 1-pentanol-cyclopentanol separation but with an extractive agent that increases the relative volatility to 1.34 for example, only 43 actual plates are required.

TABLE 1

Theoretical and Actual Plates Required vs. Relative Volatility for 1-Pentanol - Cyclopentanol Separation

| Relative Volatility | Theoretical Plates Required At Total Reflux, 99% Purity | Actual Plates Required, 75% Efficiency |
| --- | --- | --- |
| 1.15 | 66 | 88 |
| 1.20 | 51 | 68 |
| 1.24 | 43 | 57 |
| 1.26 | 40 | 53 |
| 1.34 | 32 | 43 |

OBJECTIVE OF THE INVENTION

The object of this invention is to provide a process or method of extractive distillation that will enhance the relative volatility of 1-pentanol from cyclopentanol in their separation in a rectification column. It is a further object of this invention to identify organic compounds which in addition to the above constraints, are stable, can be separated from cyclopentanol and recyled to the extractive column and reused with little decomposition.

SUMMARY OF THE INVENTION

The objects of this invention are provided by a process for separating 1-pentanol from cyclopentanol which entails the use of certain organic compounds as the agent in extractive distillation.

DETAILED DESCRIPTION OF THE INVENTION

I have discovered that certain organic compounds will greatly improve the relative volatility of 1-pentanol to cyclopentanol and permit the enhanced separation of 1-pentanol from cyclopentanol by rectification when employed as the agent in extractive distillation. Table 2 lists the compounds that I have found to be effective. They are ethylene glycol propylene glycol, 1,2-butanediol, 1,3-butanediol, 1,4-butanediol, 2,3-butanediol, 2-methyl-1,3-propanediol, 1,5-pentanediol, 1,6-hexanedio diethylene glycol, triethylene glycol, tetraethylene glycol, polyethyle glycol 400, 1,2,6-trihydroxyhexane, glycerine, sulfolane and dimethylsulfoxide.

TABLE 2

Effective Extractive Distillation Agents

| Compounds | Relative Volatility |
| --- | --- |
| None | 1.15 |
| Ethylene glycol | 1.34 |
| Propylene glycol | 1.19 |
| 1,2-Butanediol | 1.23 |
| 1,4-Butanediol | 1.20 |
| 1,3-Butanediol | 1.23 |
| 2,3-Butanediol | 1.19 |
| 2-Methyl-1,3-propanediol | 1.21 |
| 1,5-Pentanediol | 1.20 |
| 1,6-Hexanediol | 1.26 |
| Diethylene glycol | 1.21 |
| Triethylene glycol | 1.21 |
| Tetraethylene glycol | 1.19 |
| Polyethylene glycol 400 | 1.20 |
| 1,2,6-Trihydroxyhexane | 1.21 |
| Glycerine | 1.24 |
| Sulfolane | 1.24 |
| Dimethylsulfoxide | 1.19 |

THE USEFULNESS OF THE INVENTION

The usefulness or utility of this invention can be demonstrated by referring to the data presented in Tables 1 and 2. All of the successful agents show that 1-pentanol can be separated from cyclopentanol by means of extractive distillation in a rectification column and that the ease of separation as measured by relative volatility is considerable.

WORKING EXAMPLES

EXAMPLE 1

One hundred grams of a mixture comprising 75% 1-pentanol, 25% cyclopentanol and fifty grams of 1,6-hexanediol were charged to a vapor-liquid equilibrium still and refluxed five hours. Analysis indicated a vapor composition of 78.3% 1-pentanol, 21.7% cyclopentanol; a liquid composition of 74.1% 1-pentanol, 25.9% cyclopentanol. This is a relative volatility of 1-pentanol to cyclopentanol of 1.26.

EXAMPLE 2

A solution comprising 200 grams of 60% 1-pentanol, 40% cyclopentanol was placed in the stillpot of a 7.3 theoretical plate glass perforated plate rectification column. Ethylene glycol as the extractive agent was pumped in continuously. The overhead temperature was 131° C. and the stillpot temperature was 190° C. After 1.5 hours of steady operation, overhead and stillpot samples were taken and analysed The overhead composition was 88.4% 1-pentanol, 11.6% cyclopentanol and the stillpot composition was 47.5% 1-pentanol, 52.5% cyclopentanol. This gives a relative volatility of 1-pentanol to cyclopentanol of 1.34

I claim:

1. A method for recovering 1-pentanol from a mixture of 1-pentanol and cyclopentanol which comprises distilling a mixture of 1-pentanol and cyclopentanol in the presence of about one part of an extractive agent per part of 1-pentanol - cyclopentanol mixture, recovering the 1-pentanol as overhead product and obtaining the cyclopentanol and the extractive agent from the stillpot, wherein said extractive agent consists of one material selected from the group consisting of ethylene glycol, propylene glycol, 1,2-butanediol, 1,3-butanediol, 1,4butanediol, 2,3-butanediol, 2-methyl-1,3-propanediol, 1,5-pentanediol, 1,6-hexanediol, diethylene glycol, triethylene glycol, tetraethylene glycol, polyethylene glycol 400, 1,2,6-trihydroxyhexane, glycerine, sulfolane and dimethylsulfoxide.

* * * * *